United States Patent
Matteo et al.

(10) Patent No.: US 12,247,048 B2
(45) Date of Patent: Mar. 11, 2025

(54) PROCESS FOR THE PREPARATION OF CORTEXOLONE 17α-PROPIONATE AND NEW HYDRATED CRYSTALLINE FORM THEREOF

(71) Applicant: FARMABIOS S.P.A., Gropello Cairoli (IT)

(72) Inventors: Ponzinibi Matteo, Lodi (IT); Roberto Arosio, Civate (IT); Brusasca Marco, Valenza (IT); Di Giacomo Mario, Cenate Sotto (IT)

(73) Assignee: Farmabios S.P.A. (IT)

( * ) Notice: Subject to any disclaimer, the term of this patent is extended or adjusted under 35 U.S.C. 154(b) by 0 days.

(21) Appl. No.: 17/708,159

(22) Filed: Mar. 30, 2022

(65) Prior Publication Data
US 2022/0324901 A1 Oct. 13, 2022

(30) Foreign Application Priority Data
Apr. 6, 2021 (IT) .................. 102021000008429

(51) Int. Cl.
*C07J 5/00* (2006.01)

(52) U.S. Cl.
CPC ......... *C07J 5/0053* (2013.01); *C07B 2200/13* (2013.01)

(58) Field of Classification Search
CPC ............................ C07J 5/0053; C07B 2200/13
See application file for complete search history.

(56) References Cited

U.S. PATENT DOCUMENTS

| | | | |
|---|---|---|---|
| 3,152,154 A | 10/1964 | Alberto et al. | |
| 2020/0155572 A1 | 5/2020 | Ajani et al. | |

FOREIGN PATENT DOCUMENTS

| | | | |
|---|---|---|---|
| CN | 101812108 B | 5/2012 | |
| CN | 101891797 B | 8/2012 | |
| CN | 103193845 B | 7/2015 | |
| CN | 112028956 A | 12/2020 | |
| EP | 1421099 B1 | 2/2005 | |
| EP | 2503005 B1 | 9/2015 | |
| GB | 996079 A | 6/1965 | |
| RU | 2156256 C1 | 9/2000 | |
| WO | 03014141 A1 | 2/2003 | |
| WO | 2009019138 A3 | 10/2009 | |

OTHER PUBLICATIONS

Search Report for IT202100008429, mailed Dec. 2, 2021.
Ferraboschi, P. et al., "Full spectroscopic characterization of two crystal pseudopolymorphic forms of the antiandrogen cortexolone 17α-propionate for topic application", Steroids, 128, http://dx.doi.org/10.1016/j.steroids.2017.09.003, Sep. 18, 2017, 95-104.
Ferraboschi, P. et al., "Lipase-catalyzed preparation of corticosteroid 17a-esters endowed with antiandrogenic activity", Tetrahedron Letters, 49, doi:10.1016/j.tetlet.2008.05.086, May 23, 2008, 4610-4612.
Gardi, R. et al., "Corticosteroid 17a -Monoesters from 17α,21-Cyclic Orthoesters", Tetrahedron Letters, 13, 1961, 448-451.
Numazawa, M. et al., "New Preparation and Controlled Alkaline Hydrolysis of 21-Bromo-20-ketopregnenes. A Facile Synthesis of Deoxycorticoids1", J. Org. Chem., 50, 1985, 81-84.
Ringold, H. J. et al., "Structure of Glycopeptides from a Human γ-Globulin", Communications to the Editor, 80, 1957, 250.

*Primary Examiner* — Barbara P Badio
(74) *Attorney, Agent, or Firm* — Elmore Patent Law Group, P.C.; Joseph C. Zucchero

(57) ABSTRACT

The present invention is directed to a process for the preparation of cortexolone 17α-propionate, comprising a hydrolysis reaction of an ortho-ester of formula (III)

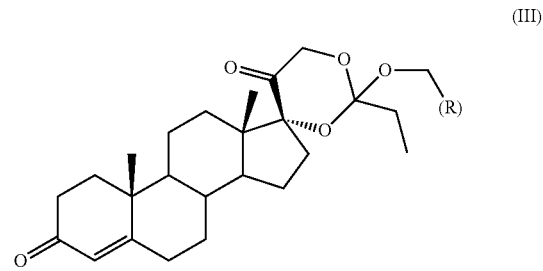

(III)

in which R is a hydrogen atom or a methyl group,
in the presence of a dilute solution of acetic acid.
The present invention is also directed to a hydrated crystalline form of cortexolone 17α-propionate obtained by such process.

1 Claim, 3 Drawing Sheets

PROCESS FOR THE PREPARATION OF CORTEXOLONE 17α-PROPIONATE AND NEW HYDRATED CRYSTALLINE FORM THEREOF

The present invention is directed to a process for the preparation of cortexolone 17α-propionate, comprising a hydrolysis reaction of an ortho-ester of formula (III)

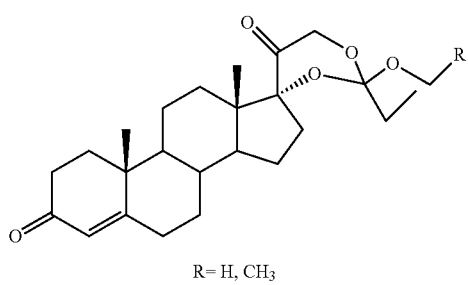

(III)

R= H, CH₃ in the presence of a dilute solution of acetic acid.

The present invention is also directed to a hydrated crystalline form of cortexolone 17α-propionate obtained by this process.

Cortexolone 17α-propionate is a steroid antiandrogen used for the topical treatment of androgen-dependent skin conditions, such as acne, hirsutism or androgenetic alopecia.

The active ingredient cortexolone 17α-propionate, also known as clascoterone or 17α, 21-dihydroxypregn-4-en-3, 20-dione 17α-propionate, has the following formula (I):

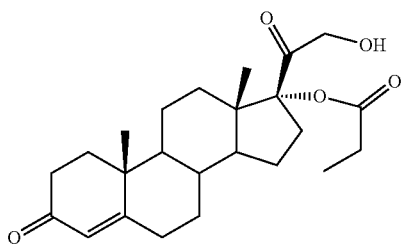

(I)

and is commercialized as medicine in the form of cream, gel or unguent for topical application under the brand name WINLEVI®.

Several processes for the preparation of cortexolone 17α-propionate are known in the art.

For example, U.S. Pat. No. 3,152,154 discloses a process for the preparation of cortexolone 17α-propionate which involves the transformation of cortexolone into the corresponding ortho-ester by reaction with an alkyl ester of an orthocarboxylic acid, under acid catalysis (e.g. PTSA). The subsequent hydrolysis, carried out in an acidic, mineral or organic medium, in an alcoholic medium, yields the desired 17-monoester. This route of synthesis is reported in Scheme 1 below:

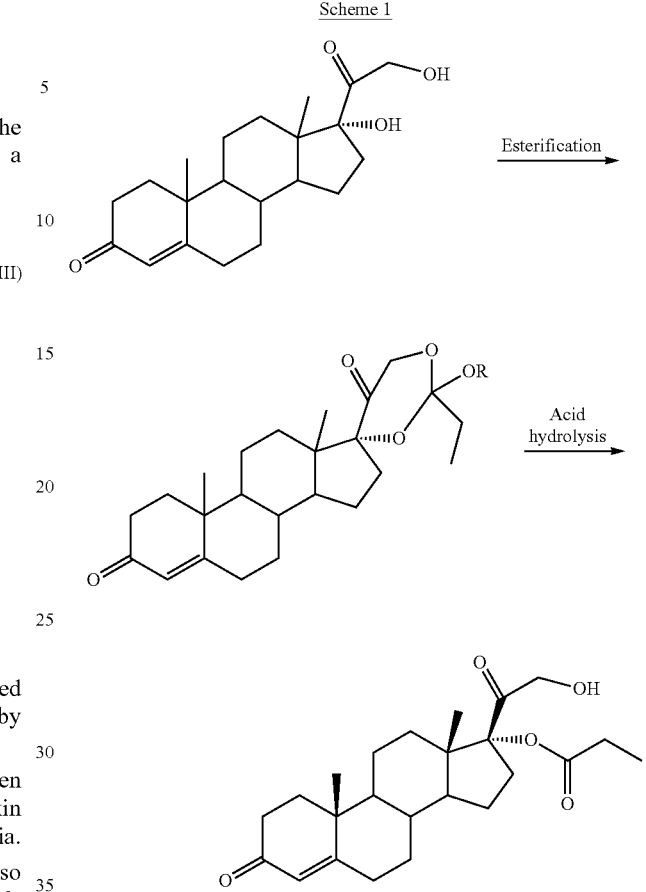

Scheme 1

However, it has been observed that, under these reaction conditions, during the hydrolysis of 17,21-ortho-esters, in addition to the desired 17-monoester product, an amount of about 10% of the corresponding 21-monoester is formed both as primary product reaction and by transposition of the 17-monoester, as disclosed in Tetrahedron Letters, 1961, p. 448.

In order to isolate the 17-monoester it is necessary to resort, at the end of the synthesis, to a purification process through accurate fractional crystallization or column chromatography procedures, with consequent and inevitable loss of product. In addition, the acid hydrolysis reaction takes place in very short times (5-10 minutes) which do not allow an industrial application of the process due to the subsequent formation of reaction by-products such as the formation of the 21-monoester or the complete hydrolysis of the ortho-ester to give cortexolone.

The article Tetrahedron Letters, 1961, points out the difficulty of obtaining 17-alpha monoesters given their easy tendency to rearrange to provide the corresponding 21-monoesters in quantitative yield. Furthermore, the isomerization rate decreases as the length of the acyl chain in position 17 increases.

In order to limit the transposition of the 17-monoester into the analogue 21-monoester, in CN 103193845 the use of gluconic acid is proposed to carry out the acid hydrolysis reaction. However, even with this procedure, too high a quantity of 21-monoesters is obtained and therefore further purification procedures are needed.

CN 101891797 proposes the use of a mixture of ammonium chloride and aluminum trichloride to hydrolyze the cyclic ortho-ester into the corresponding 17-monoester. With this method the amount of 21-monoester is reduced to below 3%; however, the experimental procedure requires a constant control of the pH to keep it equal to 3.

In EP 1421099 an enzymatic alcoholysis reaction is described in order to remedy the transesterification problems, improving the chemoselectivity of the reaction; however, the proposed method requires the use of enzymes, i.e. of a biocatalytic and non-chemical process that requires a different technology from that described in this application. The reaction is also reported in Tetrahedron Letters 49 (2008) 4610-4612.

CN101812108 describes a process which leads to the formation of 17α-butyrate-21-acetate hydrocortisone by reaction of cortexolone 21-acetate with butyryl chloride and subsequent basic hydrolysis with potassium carbonate at −10° C. However, the basic hydrolysis conducted on the cortexolone derivatives proved to be non-selective and resulted in a complete hydrolysis to cortexolone.

We have now found a method for the preparation of cortexolone 17α-propionate which does not have the drawbacks of the known technique and which allows the formation of 21-monoester as a reaction by-product to be reduced to a quantity stably lower than 3%, without requiring the use of procedures and reagents that make laborious their application on an industrial scale.

In fact, thanks to the method of the present invention, not only the 21-monoester is always less than 3% under the reaction conditions, but also its increase is not observed by extending the reaction time, thus making it possible to use the reaction on an industrial scale.

Figure 1:
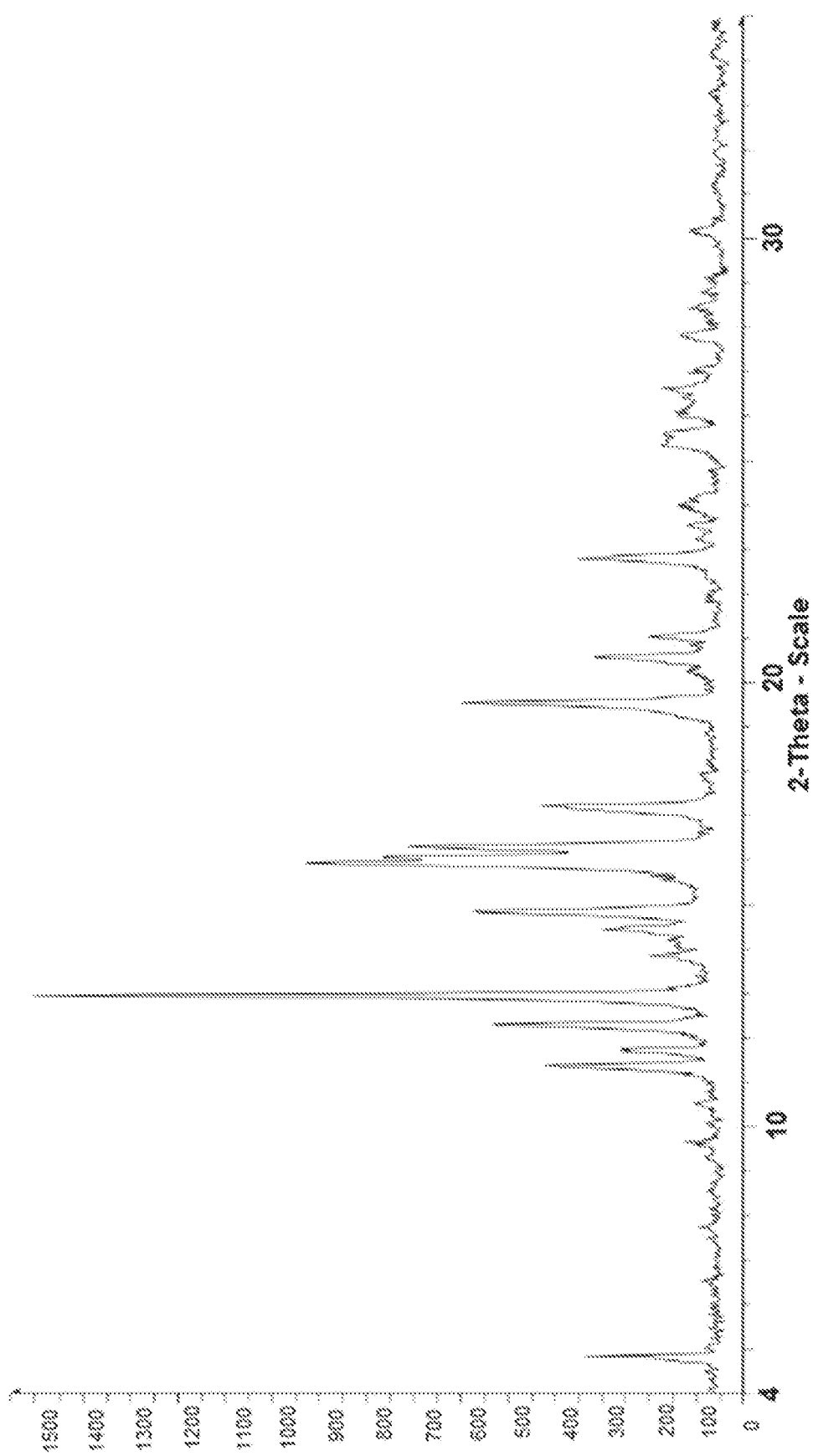
FIG. 1: XRPD of the hydrated crystalline form of cortexolone 17α-propionate obtained with the process of the present invention.

An object of the present invention is therefore a process for the preparation of cortexolone 17α-propionate of formula (I) comprising the following steps:

a) ortho-esterification of cortexolone of formula (II)

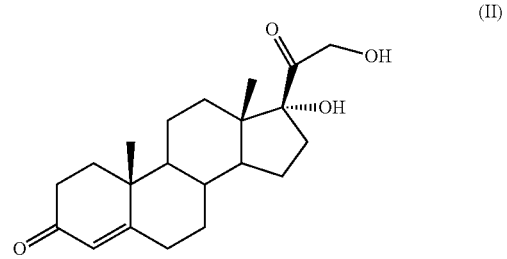 [SMILES: C[C@]12CCC(=O)C=C1CCC1C2CC[C@@]2(C)C1CC[C@]2(O)C(=O)CO]

(II)

in the presence of a reagent selected from triethyl orthopropionate and trimethyl orthopropionate to provide the corresponding ortho-ester of formula (III)

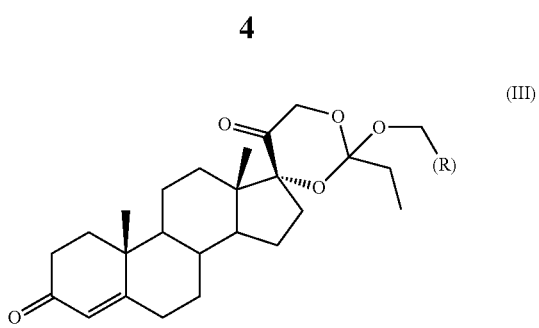

(III)

wherein R is a hydrogen atom or a methyl group b) hydrolysis of the ortho-ester of formula (III) in the presence of a dilute solution of acetic acid to provide to desired cortexolone 17α-propionate of formula (I) having a reduced content of impurities.

According to the present invention, cortexolone of formula (II) used in step a) is commercially available or is synthesized according to procedures well known to the skilled person, such as for example in Journal of the American Chemical Society (1950), 72, 5145-7, Journal of Organic Chemistry (1985), 50(1), 81-4.

Preferably, cortexolone of formula (II) is prepared by hydrolysis in basic medium of a cortexolone 21-monoester of formula (IV), according to the method disclosed for example in the Russian patent 02156256 and in Journal of the American Chemical Society (Steroids. XCIII.1 Introduction of the cortical hormone side-chain, Howard J. Ringold, 1958, 80, 1 p. 250).

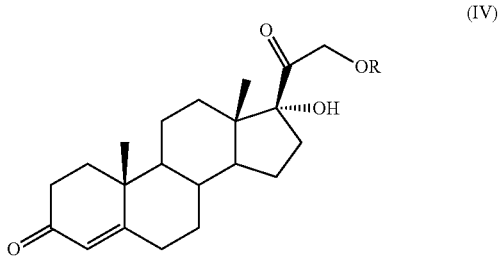

(IV)

wherein R is an acyl group $C_2$-$C_6$,

According to a particularly preferred embodiment of the present invention, cortexolone 21-monoester of formula (IV) is cortexolone 21-acetate, in which R is an acetyl group.

Such particularly preferred embodiment of the process of the present invention is represented in the scheme 2 below:

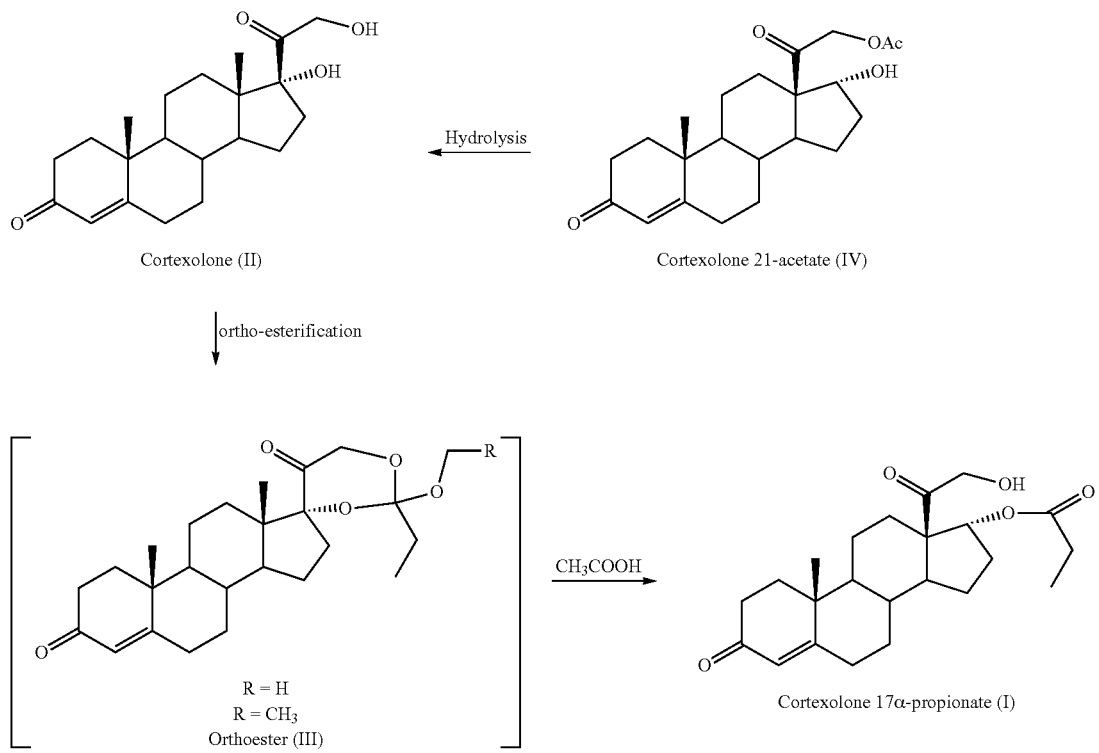

Scheme 2

The conditions for performing the hydrolysis in basic medium of cortexolone 21-monoester of formula (IV) are well known to the skilled person.

For instance, cortexolone 21-monoester of formula (IV) is dissolved in an organic solvent selected from methanol, dichloromethane and mixtures thereof. Preferably, said compound of formula (IV) is dissolved in a mixture of methanol and dichloromethane.

The resultant solution is cooled at a temperature of about −5° C. and an inorganic base is added. Examples of inorganic bases according to the present invention are sodium hydroxide, potassium hydroxide and lithium hydroxide.

One hour after addition of the base, the reaction is complete and cortexolone of formula (II) is obtained, which is then used for the reaction of ortho-esterification of step a).

According to the present invention, the cortexolone that undergoes the ortho-esterification reaction (step a) is dissolved in an organic solvent. Said organic solvent is selected from dichloromethane, dimethylformamide and mixtures thereof, preferably dichloromethane. Dissolution is conveniently carried out at room temperature.

Said ortho-esterification reaction is carried out in the presence of an ortho-ester and of a buffer consisting of an acid and a base.

Said orthoester is selected from triethyl orthopropionate, trimethyl orthopropionate, preferably triethyl orthopropionate.

Said acid is preferably p-toluensulfonic acid.

Said base is an organic base selected from pyridine, triethylamine, lutidine, preferably pyridine. Once the reaction is completed, as it is well known to the skilled person, the reaction mixture can be subjected to purification, such as chromatographic column, crystallization in order to isolate the compound of formula (III) or it can be used as such in the next step.

According to a preferred embodiment of the invention, the ortho-ester of formula (III) is not isolated and is used as such in the following step b).

The process of the present invention provides that, to the solution containing the ortho-ester of formula (III) dissolved in an organic solvent, such as methanol, ethanol, alone or mixed with water, an amount of acetic acid is added such as to create a dilute solution of acetic acid.

The acetic acid used in the process of the present invention is glacial acetic acid or 80% acetic acid. Preferably, 80% acetic acid is used.

Preferably the molar quantity of acetic acid introduced into the reaction mixture is between 0.004 equivalents and 0.007 equivalents, with respect to the quantity of ortho-ester of formula (III).

More preferably, the molar quantity of acetic acid introduced into the reaction mixture is of about 0.00625 equivalents, with respect to the quantity of ortho-ester of formula (III).

The molar concentration of acetic acid in the reaction mixture is thus preferably between $0.7 \cdot 10^{-3}$ M and $1.3 \cdot 10^{-3}$ M, more preferably is of about $1.2 \cdot 10^{-3}$ M.

The reaction takes place at a temperature between room temperature and the reflux temperature of the reaction mixture consisting of an alcoholic solvent, such as methanol, ethanol, and water, preferably the temperature is between 65° C. and 75° C., preferably 70° C., for about 1 hour and a half.

Thanks to the process of the present invention and in particular to the use of an extremely low amount of acetic acid, the Applicant was able to prepare cortexolone 17α-propionate, reducing the formation of 21-monoester in the product below 3%. The developed process is also easily achievable on an industrial level and does not require pH control.

As it is well known to those skilled in the art, the resultant cortexolone 17α-propionate can be subjected to various purification processes, such as column chromatography and crystallization. According to a preferred embodiment of the present invention, cortexolone 17α-propionate is subjected to crystallization in at least two organic solvents mixed with water.

Said at least two organic solvents are selected from acetonitrile, hexane, heptane, cyclohexane, isopropyl ether and ethyl acetate.

11.36; 11.70; 12.29; 12.95; 14.44; 14.84; 15.93; 16.09; 16.31; 17.20; 19.56; 20.58; 22.82±0.2° 2θ or as reported in FIG. 1.

Figure 2:
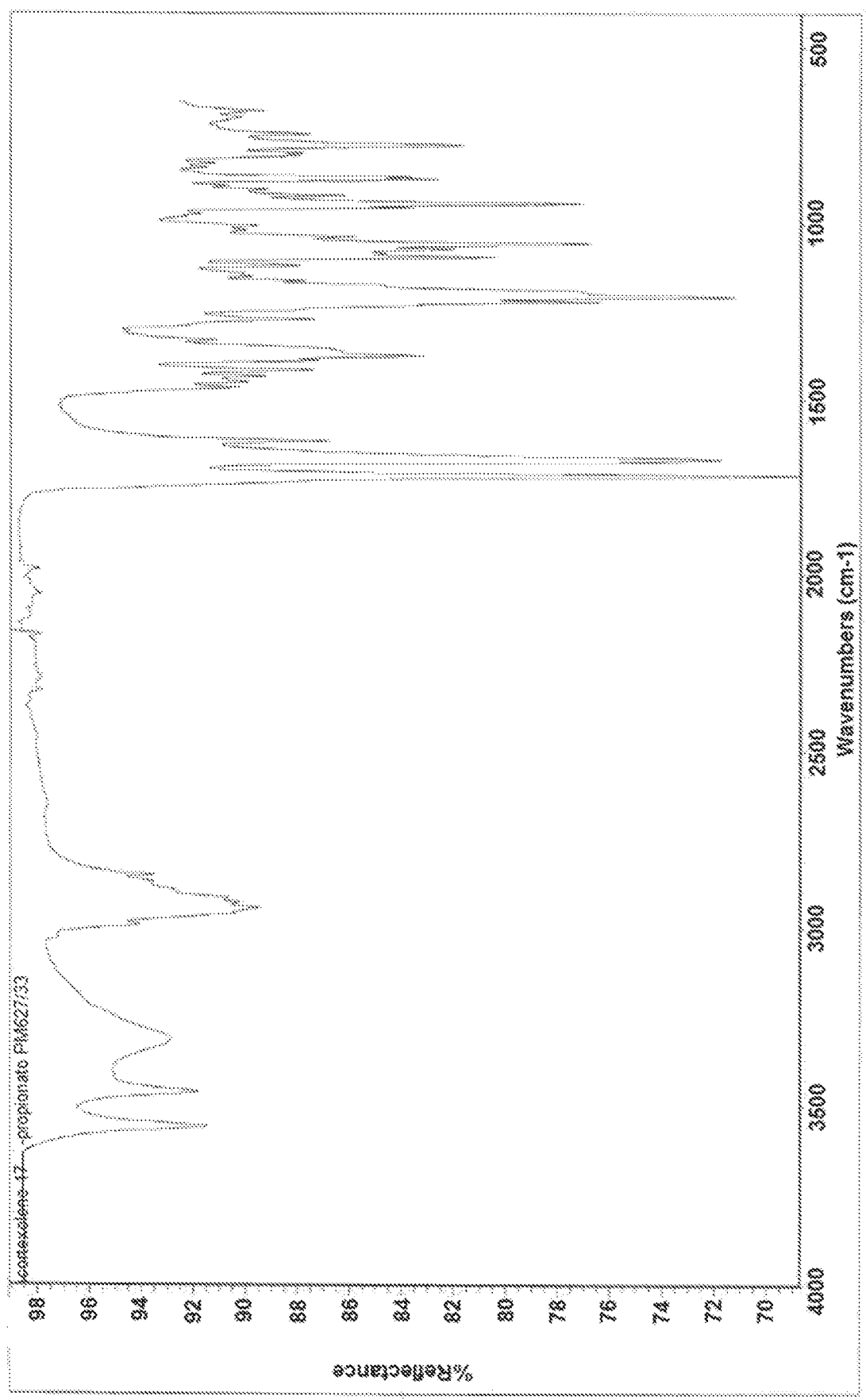
FIG. 2: IR of the hydrated crystalline form of cortexolone 17α-propionate obtained with the process of the present invention.

According to a preferred embodiment, said hydrated crystalline form has an IR spectrum as reported in FIG. 2.

Figure 3:
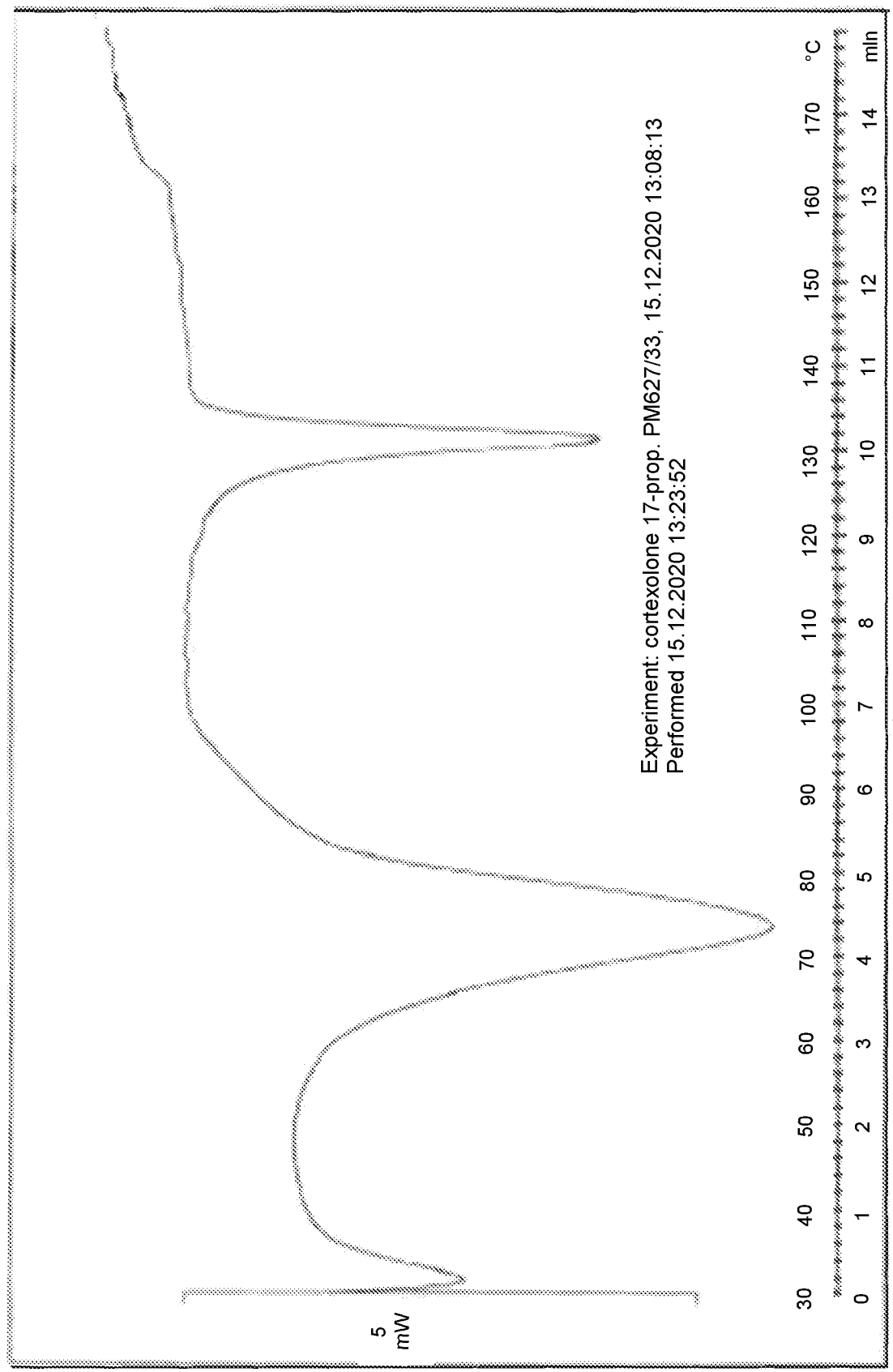
FIG. 3: DSC of the hydrated crystalline form of cortexolone 17α-propionate obtained with the process of the present invention.

According to a preferred embodiment, said hydrated crystalline form has a DSC thermogram as reported in FIG. 3.

As said above, the hydrated crystalline form of the present invention is novel with respect to the hydrated crystalline forms disclosed for example in WO 2009/019138, EP 2 503 005 and in Steroids, 2017, 128, 95-104.

Table 1 below reports the characterizing peaks 2θ of these hydrated crystalline forms of cortexolone 17α-propionate with the corresponding intensities of each peak.

TABLE 1

| Steroids 2θ | Int. | EP2503005 2θ | Int. | WO2009/019138 2θ | Int. | Hydrated form according to example 4 2θ | Int. |
|---|---|---|---|---|---|---|---|
| 4.74 | 16% | 4.64 | 38% | | | 4.80 | 22% |
| | | 6.43 | 23% | 6.18 | 38% | | |
| | | | | 10.29 | 13% | | |
| | | 11.07 | 20% | 11.17 | 12% | | |
| 11.32 | 24% | | | | | 11.36 | 28% |
| | | 11.42 | 17% | | | | |
| 11.57 | 14% | | | | | | |
| | | | | 11.76 | 24% | 11.70 | 17% |
| 12.19 | 34% | 12.14 | 27% | | | 12.29 | 35% |
| | | | | 12.64 | 72% | | |
| 12.85 | 73% | 12.85 | 73% | | | | |
| | | | | | | 12.95 | 100% |
| | | | | 13.82 | 62% | | |
| | | | | 14.11 | 83% | | |
| 14.38 | 29% | 14.28 | 60% | | | 14.44 | 20% |
| 14.73 | 53% | | | 14.71 | 49% | | |
| | | 14.99 | 51% | | | 14.84 | 38% |
| 15.79 | 100% | 15.8 | 100% | | | 15.93 | 68% |
| | | 16.07 | 85% | | | 16.09 | 51% |
| | | | | 16.17 | 100% | | |
| | | | | | | 16.31 | 47% |
| 17.06 | 44% | | | | | | |
| | | | | 17.35 | 48% | 17.20 | 28% |
| | | 17.50 | 39% | | | | |
| | | | | 17.94 | 20% | | |
| | | | | 18.82 | 29% | | |
| 19.38 | 70% | 19.28 | 64% | | | | |
| | | | | | | 19.56 | 40% |
| | | 19.64 | 70% | | | | |
| | | 20.07 | 44% | | | | |
| | | | | 20.29 | 36% | | |
| 20.52 | 50% | | | | | 20.58 | 21% |
| 20.96 | 35% | | | | | | |
| | | 21.07 | 41% | 21.17 | 25% | | |
| | | | | 22.35 | 72% | | |
| 22.76 | 38% | 22.85 | 35% | | | 22.82 | 23% |
| | | | | 23.52 | 76% | | |
| 23.90 | 25% | 23.92 | 42% | 25.00 | 36% | | |

Int.: Peak intensity

More preferably, said at least two organic solvents are acetonitrile and hexane.

In alternative, said at least two organic solvents are isopropyl ether and ethyl acetate.

The Applicant has now surprisingly found that from these mixtures, a new hydrated crystalline form of cortexolone 17α-propionate is obtained, thus providing an alternative solution to those already known in the art.

A further object of the present invention is therefore a hydrated crystalline form of cortexolone 17α-propionate characterized by the following XRPD peaks at about 4.80;

The hydrated crystalline form obtained by the process of the present invention is therefore novel since some of the characteristic peaks and the intensity maximum differ from those present in the art. The corresponding XRPD spectra are consequently not superimposable between them.

Said hydrated crystalline form can be particularly interesting from an industrial point of view in the preparation of pharmaceutical compositions containing cortexolone 17α-propionate, in particular of topical creams, which is the main use of this product, thus offering an alternative solution to those already present in the state of the art.

A further object of the present invention is thus the hydrated crystalline form of cortexolone 17α-propionate obtained by the process of the present invention.

EXPERIMENTAL PART

Example 1

Hydrolysis Cortexolone-21-acetate

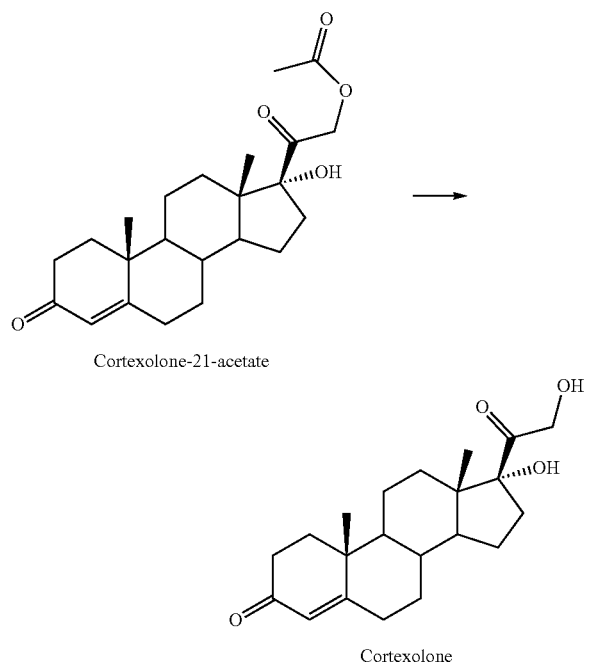

Cortexolone-21-acetate

↓

Cortexolone

Cortexolone-21-acetate (10 g) is charged in a reactor together with 60 ml of dichloromethane and 120 ml of methanol. Subsequently 1.25 ml of 30% NaOH are added at −5° C.

The reaction is stopped by adding 1 ml of 80% acetic acid.

The solvent is removed by distillation and the product of formula (II) is isolated by precipitation by adding 60 ml of water on the reaction mass, obtaining, after drying, about 9.5 g of Cortexolone (II).

Example 2

Synthesis Cortexolone-17-propionate

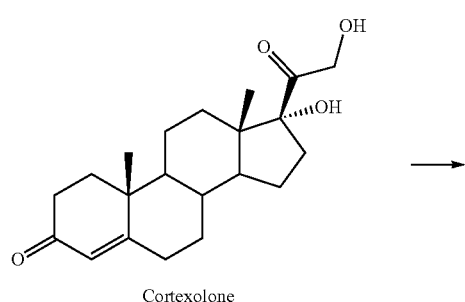

Cortexolone

↓

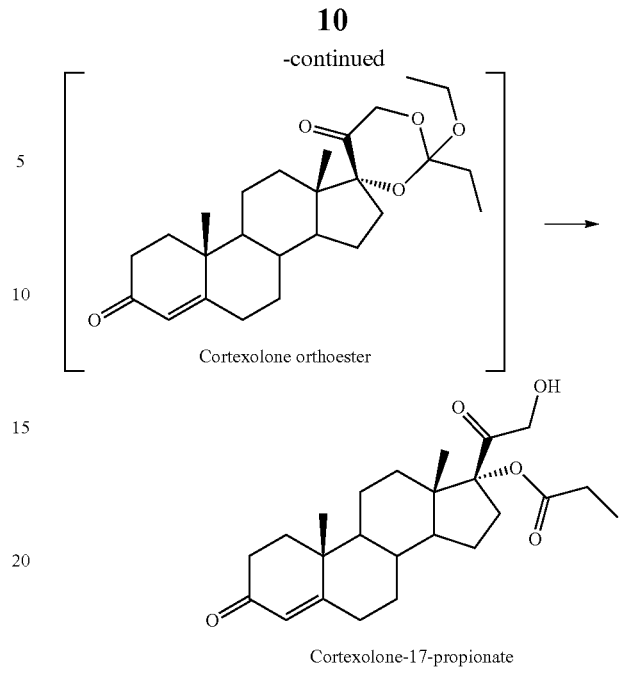

Cortexolone orthoester

↓

Cortexolone-17-propionate

A solution consisting of 2.5 ml of methylene chloride, 0.126 ml of pyridine and 268 mg of p-toluenesulfonic acid is prepared in a reaction flask which is added to the reaction mixture consisting of Cortexolone (10 g), 100 ml of methylene chloride and 11.6 ml of triethyl orthopropionate.

At the end of the reaction, 80 ml of water are added. After extraction, the organic phase solvent is removed by distillation.

The reaction mass is taken up with 80 ml of ethanol, 40 ml of water, 0.010 ml of 80% acetic acid and is brought to reflux (≈73° C.).

At the end of the reaction, the organic solvents are removed by distillation.

The residue obtained is taken up by adding 50 ml of ethyl acetate.

The two phases that are obtained are separated and the wet organic phase is then distilled under vacuum to a wet oily residue.

Example 3 (Preparation Crystalline Form)

The residue obtained in example 2 is taken up with 10 ml of ethyl acetate and heated to 50°-60° C. 80 ml of isopropyl ether are added to the solution and cooled to a temperature below 40° C. Cortexolone-17α-propionate precipitating from this solvent mixture is isolated by filtration with a yield of 75% by weight. KF: 4.03%

Example 4 (Preparation Crystalline Form)

The residue obtained in example 2 is taken up with 40 ml of acetonitrile and heated to 30°—35° C. To the solution 200 ml of hexane and 200 ml of water are added and it is cooled to a temperature below 0° C. Cortexolone-17α-propionate precipitating from this solvent mixture is isolated by filtration with a yield of 99% by weight. KF: 1.52%

The XRPD diffraction spectrum was performed using a Bruker D8 diffractometer equipped with a scintillation detector. The analysis was performed using a CuKα tube as an X-ray source. The data were collected in the angular range 5°-35° (2θ), step 0.03° and at a scanning speed of 4 s/step.

The IR spectrum was recorded using an iS10 Nicolet instrument, the spectrum was recorded from 4000 to 400 cm$^{-1}$.

DSC analyzes were recorded from 30° C. to 180° C., with an increase of 10° C./min, using a Mettler Toledo instrument.

The invention claimed is:

1. A hydrated crystalline form of cortexolone 17a-propionate of formula (I) characterized by:
   (a) the following XRPD peaks at about 4.80; 11.36; 11.70; 12.29; 12.95; 14.44; 14.84; 15.93; 16.09; 16.31; 17.20; 19.56; 20.58; 22.82±0,2° 2θ or according to FIG. 1;
   (b) the IR spectrum according to FIG. 2; or
   (c) the DSC thermogram according to FIG. 3.

* * * * *